(12) United States Patent
Logan et al.

(10) Patent No.: US 9,170,089 B2
(45) Date of Patent: Oct. 27, 2015

(54) SYSTEM AND METHOD FOR MEASURING PIPE

(71) Applicant: National Oilwell Varco, L.P., Houston, TX (US)

(72) Inventors: Kevin D. Logan, Houston, TX (US); Andres C. Rodriguez, Mobile, AL (US); Claudio Aguirre, Stafford, TX (US); Clive C. Lam, Tomball, TX (US)

(73) Assignee: National Oilwell Varco, L.P., Houston, TX (US)

( * ) Notice: Subject to any disclaimer, the term of this patent is extended or adjusted under 35 U.S.C. 154(b) by 225 days.

(21) Appl. No.: 13/691,021

(22) Filed: Nov. 30, 2012

(65) Prior Publication Data

US 2013/0160309 A1    Jun. 27, 2013

Related U.S. Application Data

(60) Provisional application No. 61/578,701, filed on Dec. 21, 2011.

(51) Int. Cl.
| | |
|---|---|
| *G01B 1/00* | (2006.01) |
| *G01B 11/00* | (2006.01) |
| *G01B 17/00* | (2006.01) |
| *G01B 11/02* | (2006.01) |
| *G01B 9/02* | (2006.01) |

(Continued)

(52) U.S. Cl.
CPC .............. *G01B 11/00* (2013.01); *G01B 11/026* (2013.01); *G01B 17/00* (2013.01); *G01B 5/0002* (2013.01); *G01B 5/0004* (2013.01); *G01B 7/12* (2013.01); *G01N 2291/044* (2013.01)

(58) Field of Classification Search
CPC ...... G01B 5/0002; G01B 5/0004; G01B 7/12; G01N 2291/044
USPC ................ 33/549; 73/622; 356/482, 485, 486
See application file for complete search history.

(56) References Cited

U.S. PATENT DOCUMENTS 2,563,254 A  *  8/1951  Lewis ........................... 324/229
3,289,468 A  *  12/1966 Van Der Veer et al. ......... 73/637

(Continued)

FOREIGN PATENT DOCUMENTS

| EP | 1045223 | 10/2000 |
|---|---|---|
| EP | 1992909 | 11/2008 |

(Continued)

OTHER PUBLICATIONS

International Search Report for PCT Patent Application No. PCT/US2012/067432 dated Mar. 14, 2013, 4 pages.

(Continued)

*Primary Examiner* — Laura Martin
*Assistant Examiner* — Rhyan C Lange
(74) *Attorney, Agent, or Firm* — JL Salazar Law Firm

(57) ABSTRACT

A system and method for measuring a pipe is provided. The system includes a frame rotatably receiving the pipe, a carriage movably positionable along the frame, a guide floatingly positionable about the carriage, at least one sensor for measuring a position of the pipe, and a measurement unit operatively linked to the sensor for collecting measurements therefrom. The guide has a mouth that receivingly engages the pipe and axially aligns therewith. The pipe is measured with the sensor(s) while moving at least one of the pipe, the carriage and the guide.

27 Claims, 7 Drawing Sheets

(51) Int. Cl.
*G01N 9/24* (2006.01)
*G01B 5/00* (2006.01)
*G01B 7/12* (2006.01)

(56) References Cited

U.S. PATENT DOCUMENTS

| | | | |
|---|---|---|---|
| 3,896,662 A * | 7/1975 | Camp et al. | 73/622 |
| 4,091,514 A * | 5/1978 | Motes-Conners et al. | 29/33 T |
| 4,218,651 A * | 8/1980 | Ivy | 324/227 |
| 4,258,318 A * | 3/1981 | Furukawa et al. | 324/220 |
| 4,599,900 A * | 7/1986 | Friedman | 73/622 |
| 5,043,663 A * | 8/1991 | Lam | 324/242 |
| 5,867,275 A | 2/1999 | Curtis, Jr. et al. | |
| 6,202,489 B1 * | 3/2001 | Beffy et al. | 73/628 |
| 6,272,762 B1 | 8/2001 | Kinast et al. | |
| 6,278,520 B1 | 8/2001 | Boyd | |
| 6,286,223 B1 * | 9/2001 | Iwamoto | 33/555.1 |
| 6,745,136 B2 | 6/2004 | Lam et al. | |
| 6,772,636 B2 | 8/2004 | Lam et al. | |
| 6,862,099 B2 | 3/2005 | Lam et al. | |
| 6,904,690 B2 | 6/2005 | Bakke et al. | |
| 6,931,748 B2 | 8/2005 | Lam et al. | |
| 7,197,837 B1 * | 4/2007 | Blanford et al. | 33/555.1 |
| 2004/0016139 A1 * | 1/2004 | Lam et al. | 33/544 |
| 2008/0277570 A1 * | 11/2008 | Saint Clair et al. | 250/231.18 |
| 2011/0072905 A1 | 3/2011 | Lam et al. | |
| 2011/0138920 A1 * | 6/2011 | Sauerland et al. | 73/627 |

FOREIGN PATENT DOCUMENTS

| | | |
|---|---|---|
| FR | 2420118 | 10/1979 |
| JP | 63008511 | 1/1988 |

OTHER PUBLICATIONS

Written Opinion for PCT Patent Application No. PCT/US2012/067432 dated Mar. 14, 2013, 8 pages.

* cited by examiner

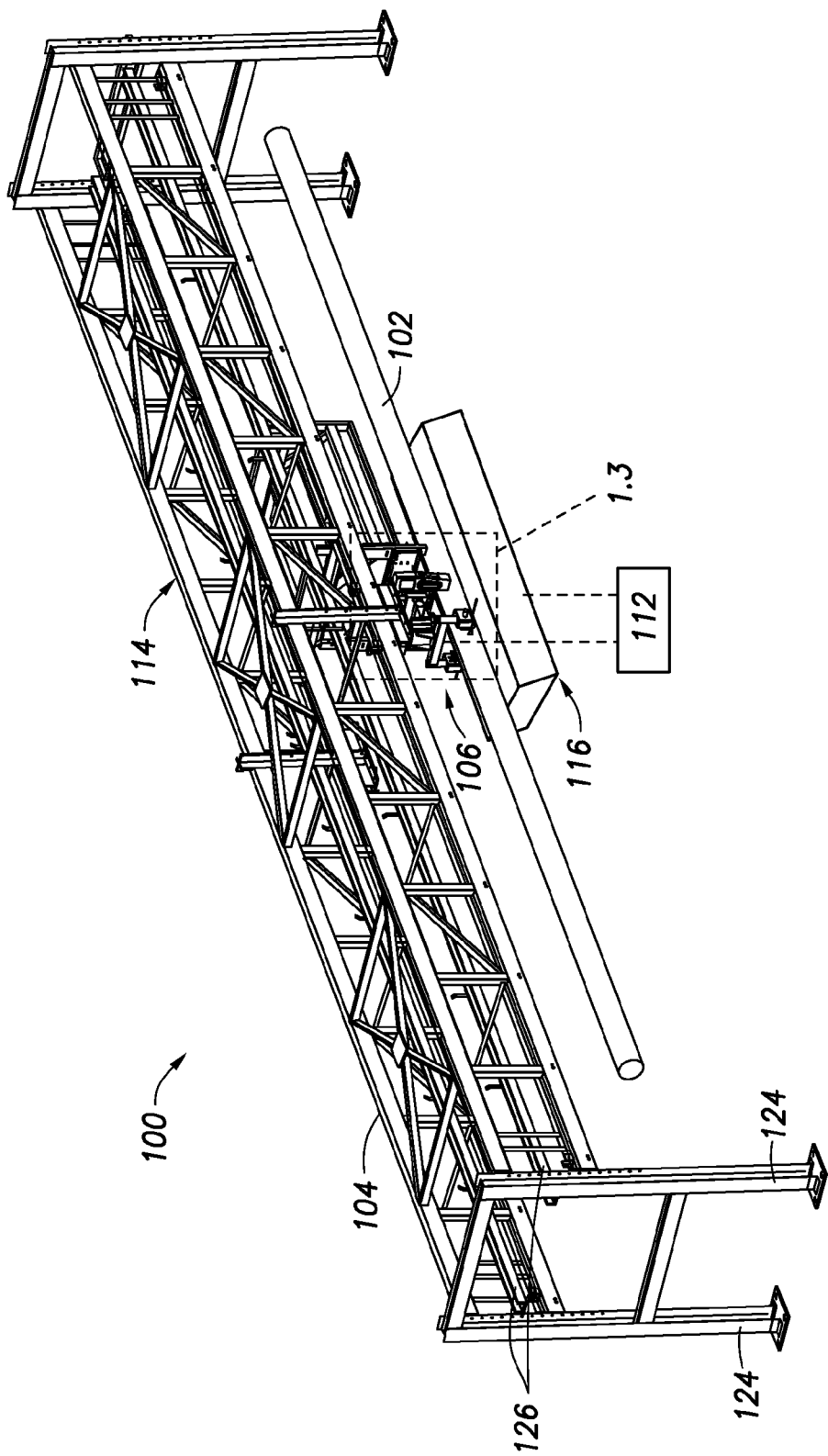
FIG.1.1

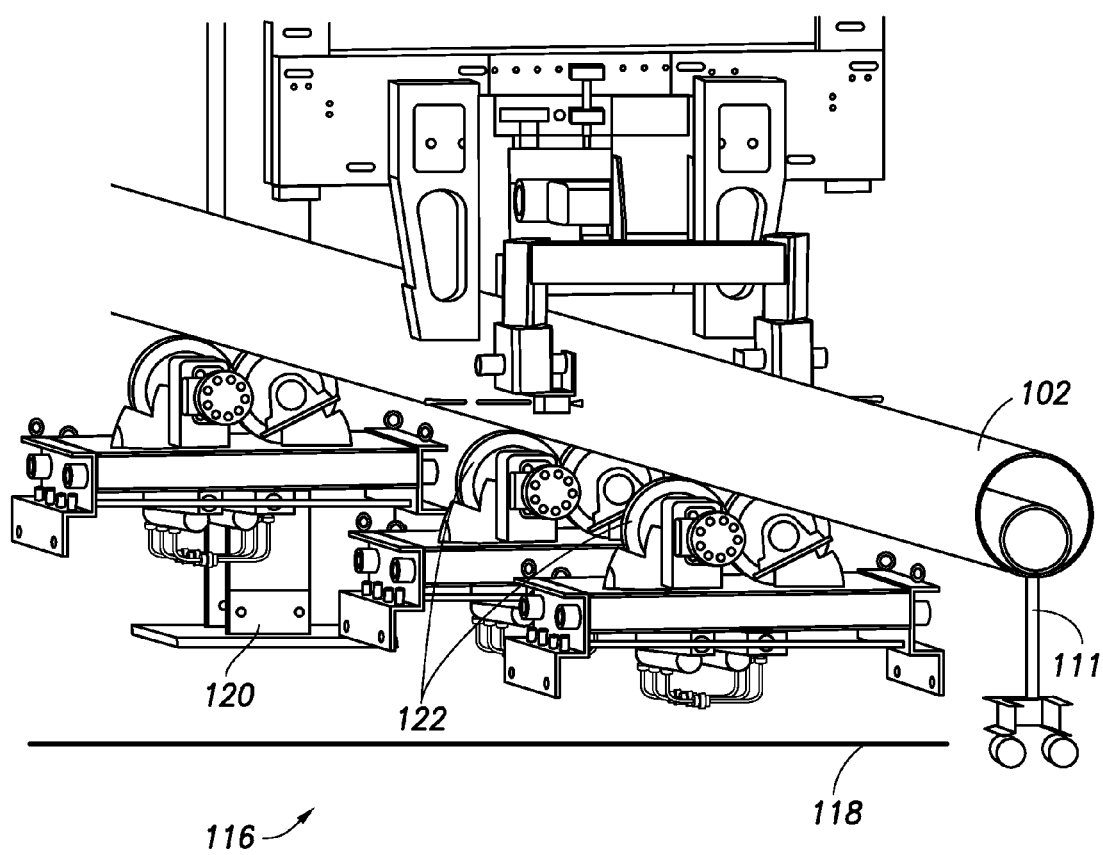
FIG.1.2

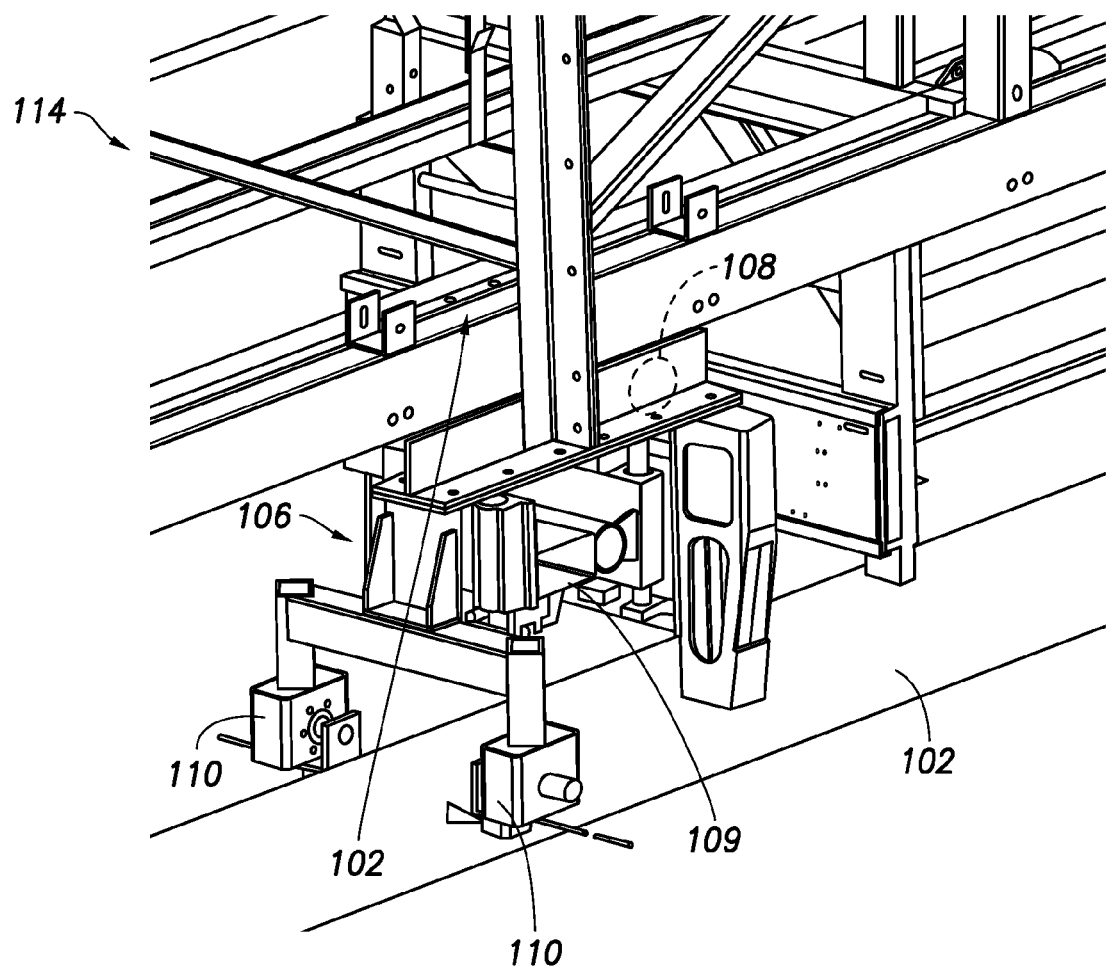
FIG.1.3

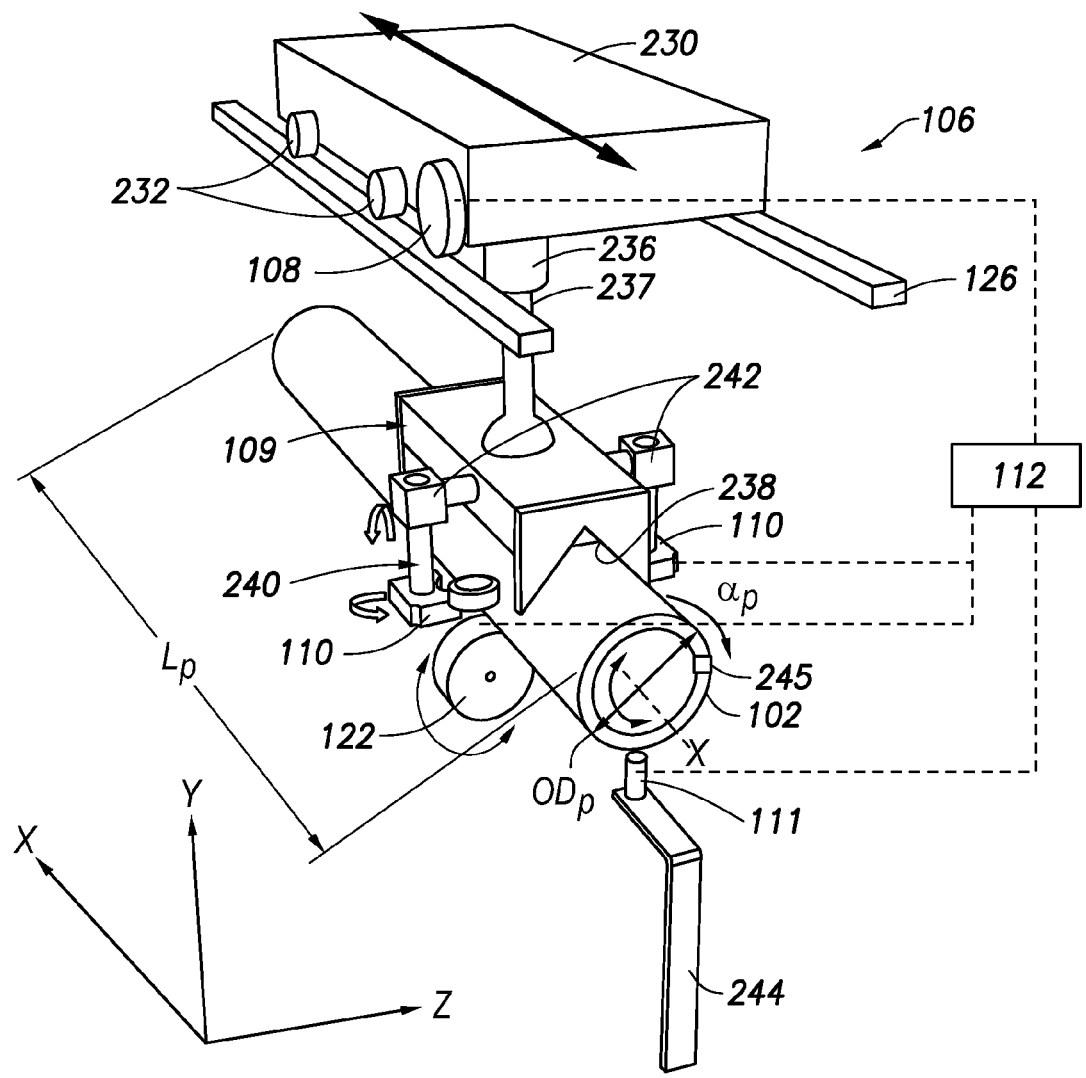
FIG.2.1

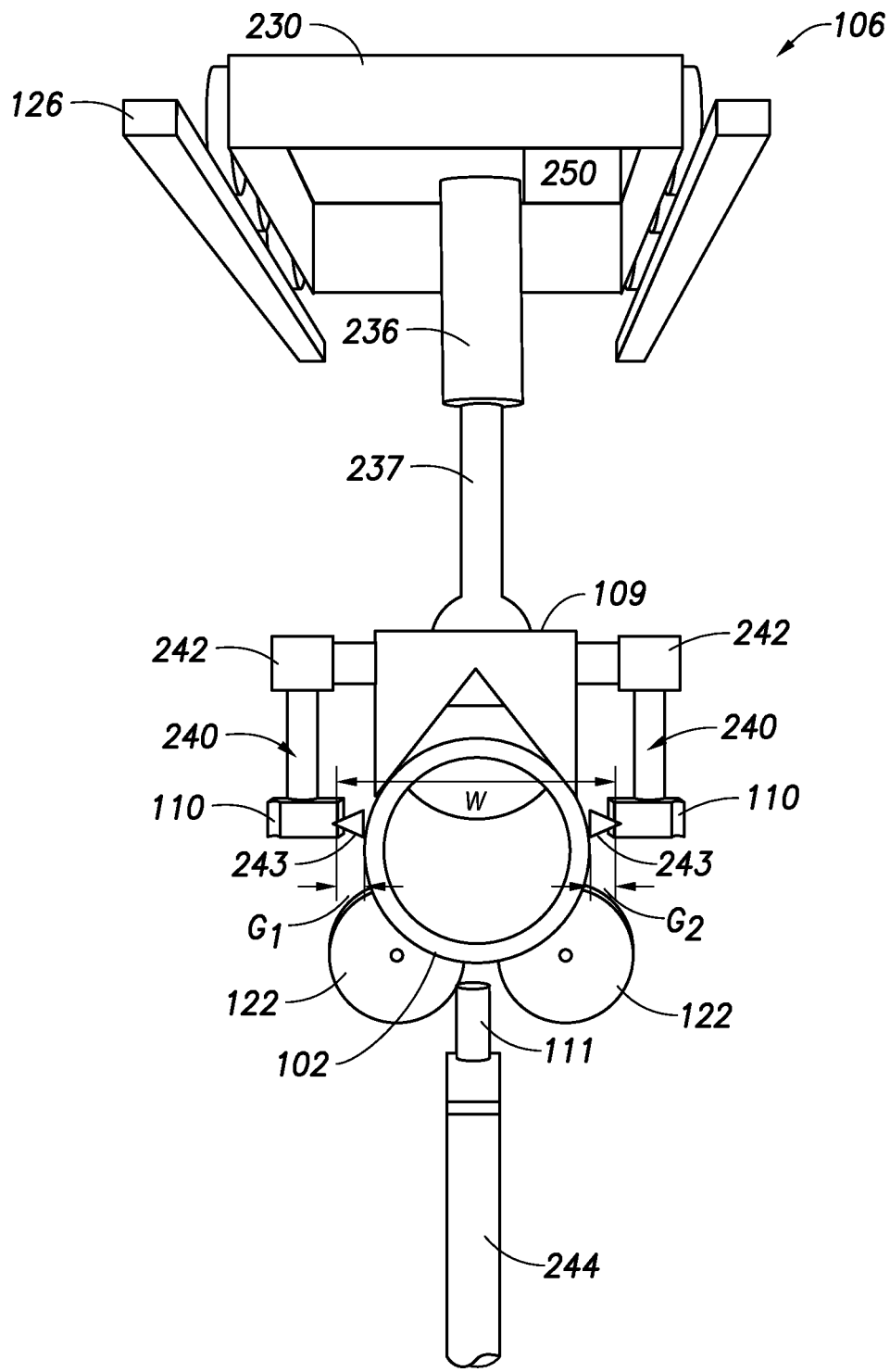
FIG.2.2

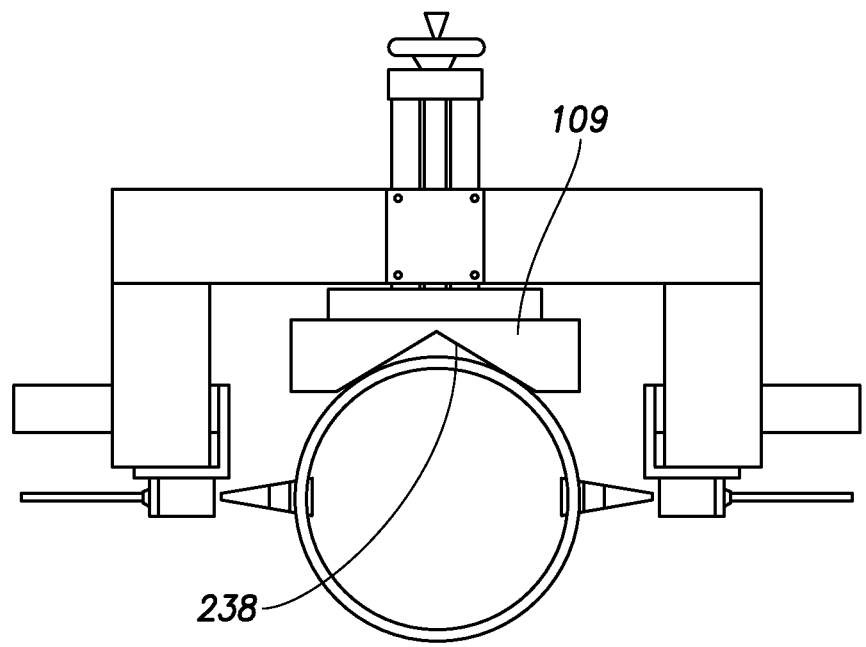
FIG.3.1
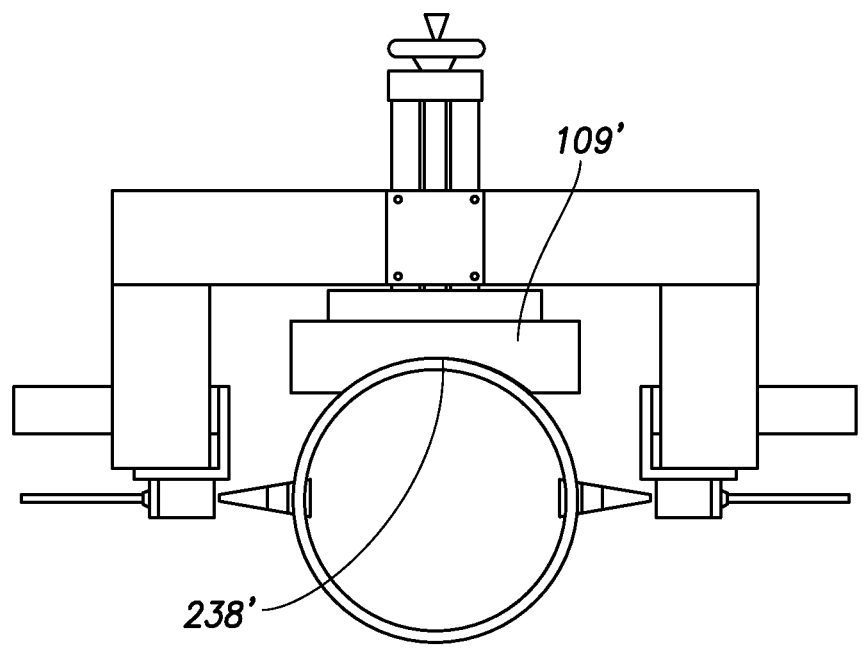
FIG.3.2

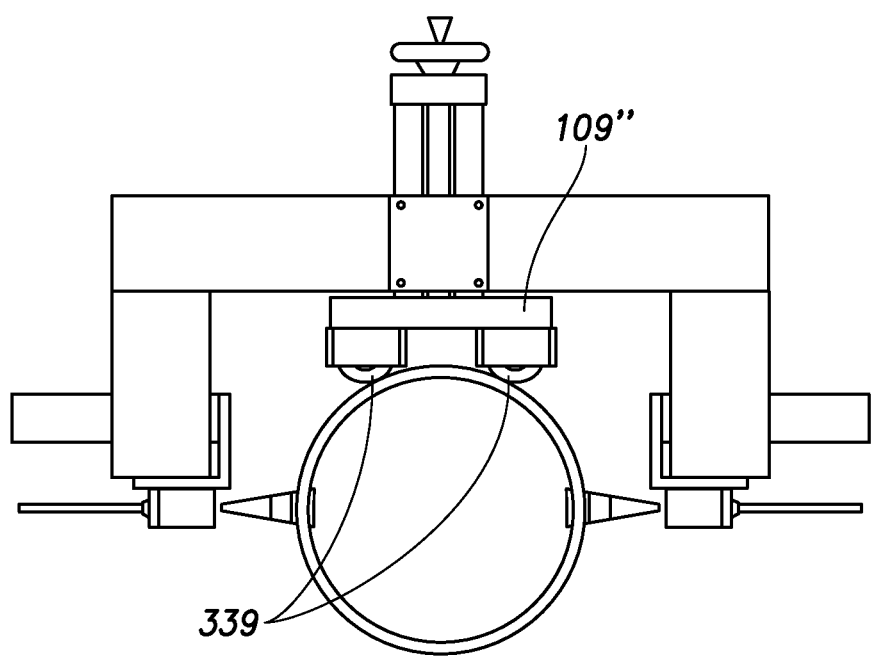
FIG.3.3

SYSTEM AND METHOD FOR MEASURING PIPE

BACKGROUND

This invention relates generally to techniques for measuring pipe. More specifically, the invention may relate to techniques for measuring dimensions, such as outer diameter of a drill pipe used in wellbore operations.

A wellbore may be drilled to reach subsurface reservoirs containing valuable hydrocarbons. To form the wellbore, a downhole drilling tool with a bit at an end thereof may be advanced into the earth. The drilling tool may be extended into the earth by threadedly connecting stands of drill pipe together to form a drill string. The quality of the drill pipe, such as the consistency of the shape (e.g., outer diameter) of the drill pipe, may affect drilling operations. Variations in shape of the drill pipe may affect, for example, rotation of the drill pipe during operation which may also affect operation of the drilling tool and/or drill bit.

Techniques have been developed to check the quality of drill pipe. In some cases, inspections of drill pipe may be performed to check, for example, full length and full body measurements. Such inspections may involve measurement of an outer diameter of the drill pipe using, for example, hand held micrometers, lasers, electronic measurement devices, sensors, etc. Measurements of the outer diameter of the drill pipe may be performed utilizing contact or non-contact methods. Examples of pipe measurement techniques may be found in US Patent/Application Nos. U.S. Pat. Nos. 6,862,099, 5,867,275, 5,043,663, 5,867,275, 6,272,762, 6,745,136, 6,772,636, 6,931,748, 6,904,690 and 2011072905.

SUMMARY

In at least one aspect, the disclosure relates to a system for measuring pipe. The system includes a frame rotatably receiving the pipe, a carriage movably positionable along the frame, a guide floatingly positionable about the carriage, at least one sensor for measuring a position of the pipe, and a measurement unit operatively linked to the sensor for collecting measurements therefrom. The guide has a mouth that receivingly engages the pipe and axially aligns therewith.

The frame has an upper and a lower portion, the lower portion having rollers rotatably receiving the pipe. The guide is floatingly suspended from the carriage. The sensor includes at least one carriage sensor detecting a position of the carriage, a plurality of guide sensors measuring displacement of the pipe, and a rotary sensor measuring a rotational position of a marker on the pipe.

In another aspect, the disclosure relates to a system for measuring pipe. The system includes a frame having an upper and lower portion, a carriage movably positionable along rails of the frame, a guide floatingly suspended from the carriage, a rotary sensor fixedly positionable about the pipe for measuring a rotational position of a marker on the pipe, and a measurement unit operatively linked to the carriage sensor. The lower portion rotatably receives the pipe. The upper portion has rails positioned a distance above the lower portion. The carriage has a carriage sensor that detects a position of the carriage along the rails. The guide has a mouth that receivingly engages the pipe and axially aligns therewith. The guide has a plurality of guide sensors positionable about the pipe and measuring a displacement thereof. The guide sensors and the rotary sensor collect measurements.

The pipe is a casing, a drill pipe, tubing, risers, or pressurized piping. The lower frame includes rollers for rotating the pipe. The carriage includes wheels for moving the carriage along the rails. The carriage includes a universal joint for floatingly supporting the guide and/or an air cylinder for floatingly supporting the guide. The mouth of the guide includes a triangular recess, at least one alignment roller, and/or a contoured recess complimentary to an outer surface of the pipe. The measurement unit includes a database and a processor. The guide sensors include lasers emitting a laser-beam on opposite sides of the pipe. The guide sensors are each supported on the guide by adjustable brackets. The carriage sensor, the plurality of guide sensors and the rotary sensor each have at least one encoder. The system also includes an ultrasonic sensor operatively connectable to the carriage for measuring parameters of the pipe and/or drive rollers on the lower portion. The measurements include an outer diameter of the pipe.

Finally, in another aspect, the disclosure relates to a method for measuring pipe. The method involves providing a system for measuring pipe. The system includes a frame rotatably receiving the pipe, a carriage movably positionable along the frame, a guide floatingly positionable about the carriage, at least one sensor for measuring a position of the pipe, and a measurement unit operatively linked to the sensor for collecting measurements therefrom. The guide has a mouth that receivingly engages the pipe and axially aligns therewith. The method also involves measuring the pipe with the at least one sensor while moving at least one of the pipe, the carriage and the guide.

The method may also involve determining an outer diameter of the pipe along a length thereof and/or determining parameters of the pipe. The method may also involve at least one of rotating the pipe about the frame, movably positioning the carriage along the frame, and engaging the pipe with the guide such that the guide is floatingly suspended thereabout.

BRIEF DESCRIPTION DRAWINGS

Embodiments of the system and method for measuring pipe are described with reference to the following figures. The same numbers are used throughout the figures to reference like features and components.

FIGS. 1.1-1.3 are schematic views of a system for measuring pipe.

FIGS. 2.1 and 2.2 are perspective and front schematic views, respectively, of a portion of the system of FIG. 1 depicting a carrier and guide.

FIG. 3.1 is another schematic view of the system depicted in FIGS. 2.2. FIGS. and 3.2 and 3.3 are schematic views of the system of FIG. 3.1 with alternate guides.

DETAILED DESCRIPTION

The description that follows includes exemplary apparatuses, methods, techniques, and instruction sequences that embody techniques of the present inventive subject matter. However, it is understood that the described embodiments may be practiced without these specific details.

The present disclosure relates to techniques for measuring a pipe, such as a casing, a drill pipe, a tubing, a riser, pressurized piping or other tubulars. The pipe may be supported on a frame, and rotated for measurement by sensors to determine, for example, outer diameter of the pipe over a length of the pipe. The sensors may be positionable about the pipe on a guide for alignment with an axis of the pipe. The sensors may be supported by devices, such as carriages and guides, that are positioned out of the way of certain equipment. The measurements may be used to verify pipe quality, to evaluate anticipated pipe performance, and/or to detect potential pipe failures (e.g., collapse), among others.

FIGS. 1.1-1.3 show a system 100 for measuring a pipe 102. The system includes a frame 104, a carriage 106, carriage sensor 108, guide 109, guide sensors 110, rotary sensors 111, and measurement unit 112. The frame 104 includes an upper portion 114 and a lower portion 116. As shown in FIG. 1.2 (and schematically shown in FIG. 1.1), the lower portion 116 is positionable on a floor 118 for movably supporting the pipe 102 thereon. The lower portion 116 has supports 120 for receiving the pipe 102, and motorized rollers 122 for rotating the pipe 102 about the lower portion 116. The pipe 102 may be positioned onto the supports 120 and/or rollers 122 using, for example, gravity feed, kick-in and kick-out arm assembly, a hoist or crane. The supports 120 and rollers 122 may be shaped and positioned to facilitate movement of the pipe 102 therealong, thereby facilitating positioning of the pipe 102 in the frame 104. The rotary sensor 111 is positionable about the lower portion 116 of the frame 104 for measuring the pipe 102 as it is rotated.

FIGS. 1.1 and 1.3 shows a portion 1.3 of the upper portion 114 of the system 100. The upper portion 114 of the frame 104 is positioned a distance above the lower portion 116 and supported on legs 124. The upper portion 114 has rails 126 extending along a length thereof. The rails 126 are configured to slidingly receive the carriage 106. The carriage 106 is movably positionable along the rails 126 for interaction with the pipe 102 positioned therebelow.

The carriage 106 has the guide 109 suspended therebelow for engaging the pipe 102. The carriage 106 has the carriage sensor 108 thereon for measuring a position of the carriage 106. The guide 109 has guide sensors 110 for measuring a gap between each guide sensor 110 to a surface of the pipe 102 as the carriage 106 translates along the rails 126. The carriage sensor 108, the guide sensors 110 and the rotary carriage sensor 111 (as well as other sensors and devices) may be operatively linked to the measurement unit 112 for capturing and/or processing measurement and/or other data collected by the various sensors. The measurement unit may also be used to control the operation of the various sensors and other equipment of the system 100.

The carriage 106 may be positioned about the upper portion 114 of the frame 104 for supporting the guide 109 adjacent the pipe 102. In this position, the guide 109 and sensors 110 are positioned a distance from the lower portion 116 of the frame 104. With the rollers 122 positioned below the pipe 102 to support and rotate the pipe 102, the carriage 106 and guide 109 may be positioned above the lower portion 116 and out of the way of the rollers 122 (and associated mechanisms) to prevent interference therewith.

While FIGS. 1.1 and 1.3 depict the carriage 106 with the guide 109 floating above the pipe 102, in some cases, other configurations may be used provided the carriage 106 and guide 109 do not interfere with the operation of the other portions of the system 100. In order to obtain outer diameter measurements of the pipe 102 over the full length and circumference of the pipe 102, either the pipe 102 rotates about the sensors (e.g., as shown in FIGS. 1.1 and 1.3) or the sensors rotate about the pipe (for example, the guide sensors may be rigidly mounted and the pipe 102 moved along the lower portion of the frame 116). In either case the sensors performing outer diameter measurements may have a clearance around the pipe 102 in order to accommodate moving parts (e.g., the rollers 122, moving sensors, lifting arms, or other rotating mechanical detectors) or a path of guide sensors 110 (e.g., light path for laser beam in the case of collimated laser beams).

In the configuration shown in FIGS. 1.1-1.3, the pipe 102 may be rotated by the rollers 122 as the carriage 106 translates back and forth along the rails 126. The guide 109 engages the pipe 102 and takes measurements with the guide sensors 110 as the guide 109 passes therealong. In some cases, the pipe may be translatable along the lower frame 116 past the guide 109 and its sensors 110 for measurement thereof. Various combinations of movement of the carriage 106, guide 109 and pipe 102 may be configured to provide the desired measurements.

FIGS. 2.1 and 2.2 schematically depict a portion of the system 100 of FIG. 1. As shown in these figures, the carriage 106 may have a body 230 with wheels 232 and the carriage sensor 108 thereon. The body 230 is movable along rails 126 via the wheels 232. The carriage 106 is axially positionable relative to an axis X of the pipe 102 by movement along the rails 126 as indicated by a linear arrow.

The carriage 106 may serve as a mounting platform for floatingly supporting the guide 109 about the pipe 102. The guide 109 is supported above the pipe 102 in an engagement position therewith as the carriage 106 translates along the rails 126 thereby moving the guide 109 along a length of the pipe 102. The carriage 106 may provide a reference defining a position along the axis X of the pipe and between the carriage 106 and the pipe 102 by means of the carriage sensor 108.

The guide 109 has a mouth 238 for receivingly engaging an outer surface of the pipe 102. As shown, the mouth 238 is a triangular shaped recess along its length that is alignably positionable adjacent the pipe 102. However, the mouth 238 may be any shape for receivingly engaging the pipe and aligning with the axis X thereof as the guide 109 moves along the pipe 102. FIG. 3.1 shows another view of the guide 109 and the mouth 238. The mouth 238 may be formed of plates at ends of the guide 109. FIGS. 3.2 and 3.3 show alternate guides and mouths that may be used. A shown in FIG. 3.2, the guide 109' may have a mouth 238' with a contoured recess complimentary to the outer surface of the pipe 102 for receipt thereof. As shown, for example, in FIG. 3.3, the guide 109" may optionally be provided with alignment rollers 339 or other alignment mechanisms for engaging and aligning the pipe 102. One or more guides 109, 109', 109" may be provided for use with the system 100. The guides 109' and 109" may function similarly to the guide 109 described herein.

Referring back to FIGS. 2.1 and 2.2, the guide 109 is positionable about the pipe 102 for floating engagement therewith as the carriage 206 translates along the rails 126. The guide 109 may be connected to the body 230 by a connector 236. The connector 236 may include, for example, a universal joint (or other device) for allowing movement of the guide 109 in various directions, such as X and Z planes (e.g., as represented on the axis of FIG. 2.1). An air cylinder 237 may also be provided to allow movement of the guide relative to the carriage 106. The connector 236 and/or air cylinder 237 may be sufficiently flexible to permit movement of the guide 109 into alignment with the axis X of the pipe 102.

The shape of the mouth 238 of the guide 109 allows the guide to conform to the shape of the pipe 102. The flexible connector 236 and air cylinder 237 allow the guide 109 to self-adjust with the freedom of movement in the X and Z axes such that the mouth 238 aligns with the axis X of the pipe 102. The guide 109 may be used to provide freedom of movement that allows the system to adjust for potential misalignments or variations in portions of the system 100 and/or pipe 102.

The guide sensors 110 are positioned on either side of the guide 109. The guide sensors 110 may be movably supportable about the guide 109 by brackets 240. The brackets 240 may have joints 242 to permit adjustable positioning of the guide sensors 110 as indicated by the arrows. The guide sensors 110 may be, for example, lasers (or light emitting diodes (LEDs)) for measuring a position or displacement of the pipe 102 as the guide sensors 110 move about the pipe 102. The lasers 110 may emit a laser beam 243 which may be used to measure curvature, circumference, radius and other pipe parameters. The laser beams 243 may be emitted in a vertical plane on opposite sides of the pipe 102 to provide continuous analog measurements that may be used to measure a minimum gap $G_1$ and $G_2$ between each laser 110 and the pipe 102. The lasers 110 may be zeroed and/or calibrated to provide proper alignment and/or to prevent errors that may exist if the plane of the laser is off or if vertical alignment is incorrect. While the lasers 110 for emitting the laser beam 243 are depicted, other devices may also be used that are capable of measuring the pipe parameters.

The guide sensors 110 may have an error due to, for example, misalignment. The floating configuration of the guide 109 may be used to adjust the guide sensors 110 and reduce potential measurement errors that may be induced by misalignments in the system 100 (e.g., rails 126 may not be perfectly parallel with the X axis and/or the height of the guide sensors 110 relative to the centerline X of the pipe may vary). The guide 109 may automatically align the guide sensors 110 with the X and Z axis of the pipe thereby reducing potential misalignment that may result, for example, from misalignment of the rails 126, carriage 106, guide 109, etc.

A proximity sensor, such as sensor 111 or other sensor (e.g., encoder), may detect a predetermined zero degree point on the pipe's circumference. A marker or magnet 245 may be positioned along the pipe 102 to identify the predetermined zero point. The sensor 111 may be used to detect the magnet 245 and determine, for example, a position of the magnet and/or an angle ($\alpha_p$) of measurement in time or position (e.g., circumferential) of the pipe relative to the zero point. This information gathered by the carriage sensor 108 and the guide sensors 110 may be correlated with the rotary sensor 111 to determine displacement at a given location along the pipe 102. For example, the position of the pipe 102 can be tracked and combined with the data from the carriage sensor 108 and/or guide sensors 110, and each outer diameter measurement ($OD_p$) may be mapped into a precise grid. The following equation may be used to determine the outer diameter of the pipe:

$$OD_p = W - (G1 + G2) \quad \text{(Equation 1)}$$

where W is the spacing between the two guide sensors 110.

The sensors used herein may be, for example, encoders or gap sensors, for measuring displacement (e.g., length measurement) along the pipe 102. Carriage sensor 108 may be, for example, a linear encoder mounted on the carriage 106 for measuring a linear position thereof along the rails 126. Encoders, such as carriage sensor 108, may track the position of the carriage 106 relative to the pipe ($L_p$) as it moves linearly along rails relative to the longitudinal axis X of pipe 102. Rotary sensor 111 may be mounted in a fixed location by mount 244 for sensing the marker 245 placed on the pipe representing a known azimuth position (e.g., zero degrees). The actual diameter measurement along with the linear and azimuth locations allows for a 3D map of the pipe outer diameter to be generated.

The various sensors 108, 110, 111 may be linked to the measurement unit 112 as schematically depicted. The measurement unit 112 may have data storage capabilities (e.g., a database) and processing capabilities (e.g., a processor) to track and/or log measurement and position data (e.g., linear and circumferential position of each data point acquired). The measurement unit may also have a controller, such as a programmable logic controller, for sensing signals to activate certain portions of the system 100.

Due to the size and weight of the product being inspected, the mechanical equipment used to handle the pipe and the inherent tendency of pipe 102 to be bent to varying degrees, tolerances may be difficult to achieve and maintain. The system 100 may be used to track the pipe independently of the carriage 106 which may be supporting other inspection assemblies, such as an ultrasonic sensor 250.

It will be appreciated by those skilled in the art that the techniques disclosed herein can be implemented for automated/autonomous applications via software configured with algorithms to perform the desired functions. These aspects can be implemented by programming one or more suitable general-purpose computers having appropriate hardware. The programming may be accomplished through the use of one or more program storage devices readable by the processor(s) and encoding one or more programs of instructions executable by the computer for performing the operations described herein. The program storage device may take the form of, e.g., one or more floppy disks; a CD ROM or other optical disk; a read-only memory chip (ROM); and other forms of the kind well known in the art or subsequently developed. The program of instructions may be "object code," i.e., in binary form that is executable more-or-less directly by the computer; in "source code" that requires compilation or interpretation before execution; or in some intermediate form such as partially compiled code. The precise forms of the program storage device and of the encoding of instructions are immaterial here. Aspects of the invention may also be configured to perform the described functions (via appropriate hardware/software) solely on site and/or remotely controlled via an extended communication (e.g., wireless, internet, satellite, etc.) network.

While the embodiments are described with reference to various implementations and exploitations, it will be understood that these embodiments are illustrative and that the scope of the inventive subject matter is not limited to them. Many variations, modifications, additions and improvements are possible. For example, various connectors and/or sensors may be used with the system.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A system for measuring pipe, the system comprising:
a frame to rotatably receive the pipe;
a carriage movably positionable along the frame;
a guide floatingly positionable about the carriage, the guide having a mouth that receivingly engages the pipe and axially aligns therewith;
a plurality of guide sensors to measure a position of the pipe, the plurality of guide sensors comprising a laser to measure a displacement between the plurality of guide sensors and the pipe; and
a measurement unit operatively linked to the plurality of guide sensors to collect measurements therefrom.

2. The system of claim 1, wherein the frame has an upper and a lower portion, the lower portion having rollers rotatably receiving the pipe.

3. The system of claim 1, wherein the guide is floatingly suspended from the carriage.

4. The system of claim 1, further comprises at least one carriage sensor to detect a position of the carriage, and a rotary sensor to measure a rotational position of a marker on the pipe.

5. A system for measuring pipe, the system comprising:
- a frame having an upper and lower portion, the lower portion to rotatably receive the pipe, the upper portion having rails positioned a distance above the lower portion;
- a carriage movably positionable along rails of the frame, the carriage having a carriage sensor that detects a position of the carriage along the rails;
- a guide floatingly suspended from the carriage, the guide having a mouth to receivingly engage the pipe and axially align therewith;
- a plurality of guide sensors positionable about the pipe, the plurality of guide sensors comprising a laser to measure a displacement between the plurality of guide sensors and the pipe;
- a rotary sensor fixedly positionable about the pipe to measure a rotational position of a marker on the pipe; and
- a measurement unit operatively linked to the carriage sensor, the plurality of guide sensors and the rotary sensor to collect measurements therefrom.

6. The system of claim 5, wherein the pipe is one of a casing, a drill pipe, tubing, risers, and pressurized piping.

7. The system of claim 5, wherein the lower portion comprises rollers to rotate the pipe.

8. The system of claim 5, wherein the carriage comprises wheels to move the carriage along the rails.

9. The system of claim 5, wherein the carriage comprises a universal joint to floatingly support the guide.

10. The system of claim 5, wherein the carriage comprises an air cylinder to floatingly support the guide.

11. The system of claim 5, wherein the mouth of the guide comprises a triangular recess.

12. The system of claim 5, wherein the mouth of the guide comprises at least one alignment roller.

13. The system of claim 5, wherein the mouth of the guide comprises a contoured recess complimentary to an outer surface of the pipe.

14. The system of claim 5, wherein the measurement unit comprises a database and a processor.

15. The system of claim 5, wherein each of the lasers emit a laserbeam on opposite sides of the pipe.

16. The system of claim 5, wherein the plurality of guide sensors is supported on the guide by adjustable brackets.

17. The system of claim 5, wherein the carriage sensor, the plurality of guide sensors and the rotary sensor each comprise at least one encoder.

18. The system of claim 5, further comprising an ultrasonic sensor operatively connectable to the carriage to measure parameters of the pipe.

19. The system of claim 5, further comprising drive rollers on the lower portion thereof.

20. The system of claim 5, wherein the measurements comprise an outer diameter of the pipe.

21. A method for measuring pipe, comprising:
- providing a system to measure the pipe comprising:
  - a frame rotatably receiving the pipe;
  - a carriage movably positionable along the frame;
  - a guide floatingly positionable about the carriage, the guide having a mouth that receivingly engages the pipe and axially aligns therewith;
  - a plurality of guide sensors comprising a laser to measure a displacement between the plurality of guide sensors and the pipe; and
  - a measurement unit operatively linked to the at least one sensor to collect measurements therefrom;
- measuring the pipe with the plurality of guide sensors while moving at least one of the pipe, the carriage and the guide.

22. The method of claim 21, further comprising determining an outer diameter of the pipe along a length thereof.

23. The method of claim 21, further comprising determining parameters of the pipe.

24. The method of claim 21, further comprising at least one of rotating the pipe about the frame, movably positioning the carriage along the frame, and engaging the pipe with the guide such that the guide is floatingly suspended thereabout.

25. The system of claim 1, wherein the plurality of guide sensors are on opposites sides of the pipe.

26. The system of claim 1, wherein the plurality of guide sensors are aligned with a diameter of the pipe.

27. The system of claim 1, wherein each of the laser of each of the plurality of guide sensors comprises an encoder to measure the displacement of the laser to the pipe.

* * * * *